United States Patent
Torkelson (10) Patent No.: US 6,997,314 B2
(45) Date of Patent: Feb. 14, 2006

(54) COVER FOR A WRITING UTENSIL AND METHODS OF ENCLOSING A WRITING UTENSIL IN A PLURALITY OF COVERS

(76) Inventor: Wendy M. Torkelson, 7857 Elmore Rd., Fruitland, ID (US) 83619

(*) Notice: Subject to any disclaimer, the term of this patent is extended or adjusted under 35 U.S.C. 154(b) by 0 days.

(21) Appl. No.: 10/831,921

(22) Filed: Apr. 26, 2004

(65) Prior Publication Data

US 2005/0236291 A1  Oct. 27, 2005

(51) Int. Cl.
*B65D 85/28* (2006.01)

(52) U.S. Cl. .................................................. 206/371
(58) Field of Classification Search ............... 206/367, 206/368, 371, 438, 440, 443, 471, 305, 306, 206/484, 486; 401/52, 88
See application file for complete search history.

(56) References Cited

U.S. PATENT DOCUMENTS

| | | | | |
|---|---|---|---|---|
| 2,066,992 A | * | 1/1937 | Matson | 281/30 |
| 2,931,495 A | * | 4/1960 | Stratton, Jr. | 206/214 |
| 3,503,492 A | * | 3/1970 | Marsh | 206/214 |
| 3,809,228 A | | 5/1974 | Fowler | |
| 3,850,352 A | * | 11/1974 | Reiner | 224/235 |
| 4,266,667 A | * | 5/1981 | Ishigaki | 206/214 |
| 5,069,337 A | * | 12/1991 | Bala | 206/306 |
| 5,228,851 A | | 7/1993 | Burton | |
| 5,332,092 A | | 7/1994 | Fischer | |
| 6,311,839 B1 | * | 11/2001 | Lo | 206/371 |
| 6,446,803 B1 | * | 9/2002 | McKinney | 206/371 |

\* cited by examiner

*Primary Examiner*—Luan K. Bui
(74) *Attorney, Agent, or Firm*—Charles R. Clark (57) ABSTRACT

A writing utensil cover is preferably made from two flexible plastic walls for use in shielding an environment from nearly all of a writing utensil having a writing tip except for the writing tip. The cover has a generally tubular shape and preferably a plurality of covers is used with the writing utensil to further reduce the potential for cross contamination by or to the writing utensil.

13 Claims, 7 Drawing Sheets

COVER FOR A WRITING UTENSIL AND METHODS OF ENCLOSING A WRITING UTENSIL IN A PLURALITY OF COVERS

CROSS-REFERENCE TO RELATED APPLICATIONS

Not applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

In modern society, health care and dental care workers, scientific laboratory workers, and myriad others often strive to preserve an environment in as sterile and uncontaminated a condition as possible in ongoing efforts to lessen contamination from one object to another.

Efforts are made by doctors, nurses, technicians, and other health care workers to guard against infection and efforts are made to create and preserve sterile environments and sterile fields in hospital and health care facilities and emergency health care environments, such as intensive care units, operating rooms, x-ray units, examination rooms, laboratories, emergency rooms, emergency response units, and ambulances. Sterile packaging for many health care goods and equipment is often encountered.

Various devices are used to package, shield or otherwise minimize cross contamination. In a typical hospital, a person can find many examples of sterile containers and bags made out of flexible plastic materials.

Dental workers including dentists also strive to lessen transmission of disease and contamination from one patient to another by sterilizing dental instruments and using antifomitic covers on various pieces of dental equipment.

Other people also are interested in lessening cross contamination in places such as industrial clean rooms, industrial and scientific laboratories, and various manufacturing production facilities.

Most if not all of the preceding people from time to time have used and will continue to use writing utensils (commonly ball point pens) in their environments. An object of the present invention is to lessen the likelihood of substantial contamination of an environment by a writing utensil or of a writing utensil by an environment.

A further object of the invention is to provide a system for helping prevent the transmission of infection and/or disease via a contaminated writing utensil having a writing tip from one patient to another patient by isolating the writing utensil except for the writing tip in a disposable, biologically impermeable cover. Preferably, a plurality of nesting writing utensil covers are nested together and used to isolate a writing utensil except for its writing tip and after use of the covered writing utensil in an environment with a patient, the outer writing utensil cover may be removed or replaced before use of the still covered writing utensil in an environment with another patient.

Another object of the invention is to increase the awareness of people to potential avenues of cross contamination that frequently have been overlooked in the past.

The present invention relates to a novel cover, nesting covers, and methods of use of the covers to help minimize contamination between an environment and a writing utensil used by a person who interacts with the environment. The cover also permits a person to use a personally preferred writing utensil such as an expensive ball-point pen, a graduation gift or other pen or writing instrument with less chance of contamination of the writing instrument by the environment or contamination of the environment by the writing utensil. Preferably, the person uses the present invention and inserts a writing utensil into a plurality of nesting covers before introducing the writing utensil into an environment.

A further object of the invention is to minimize the portion of a writing utensil exposed to an environment to a small portion in the immediate vicinity of a writing tip of the writing utensil.

BRIEF SUMMARY OF THE INVENTION

A principal objective of this invention is to help a person who uses a writing utensil having a writing tip shield an environment from nearly all of the writing utensil. The invention is a novel writing utensil cover designed to help lessen the likelihood of cross contamination between an environment and a person's writing utensil. The cover has a generally tubular shape. When used, the cover encloses all of a writing utensil except the writing tip. Preferably, the cover is sterile before use with a writing utensil. Preferably and optimally, a plurality of covers is used to further lessen the potential for cross contamination by or to a writing utensil.

The cover may be sized in a range of sizes to accommodate the various sizes and dimensions of writing utensils common in our society, but the cover may also be sized to closely fit a particular writing utensil as more fully discussed below.

The invention helps keep writing utensils clean and uncontaminated. The invention helps raise the consciences of people to issues of potential vectors for contamination that previously may have been overlooked.

The cover is preferably made of thin flexible plastic and the designed shape of the cover is such that use of the cover with a writing utensil does not unduly impede the control of the writing utensil by a user. The cover is designed to allow close control of a covered writing utensil and to increase the comfort of the user.

A further object of the invention is making available to users a cover for writing utensils that is easy to use, is inexpensive to manufacture, and is conveniently disposable after use.

In the preferred method, a plurality of nesting writing utensil covers is used.

Additional and various other objects and advantages attained by the invention will become more apparent as the specification is read and the accompanying figures are reviewed.

DETAILED DESCRIPTION OF THE INVENTION

Referring to FIGS. 1 through 28, the present invention is a novel writing utensil cover 30. A writing utensil cover 30 is designed and made to isolate most of a writing utensil 8 from an environment to help prevent contamination to or from the writing utensil. The writing utensil 8 has a writing tip 10, a tapered portion 12 adjacent the writing tip with the tapered portion increasing in cross sectional width away from the writing tip, and an opposite top end 14 farthest away from the writing tip along the longitudinal axis of the writing utensil. The writing utensil cover 30 preferably is made from two flexible plastic walls as more fully described below.

Preferably, the writing utensil cover 30 comprises a front wall 32 having two front wall side edges 34, a front wall top edge 36, a front wall bottom edge 38, a front wall inner surface 40, and a front wall outer surface 42, the front wall 32 overlies a back wall 44; the back wall 44 having two back wall side edges 46, a back wall top edge 48, a back wall bottom edge 50, a back wall inner surface 52, and a back wall outer surface 54, the front wall 32 and the back wall 44 are aligned in facing relationship with the front wall bottom edge 38 overlying the back wall bottom edge 50, the front wall side edges 34 overlying the back wall side edges 46, and the front wall inner surface 40 facing and overlying the back wall inner surface 52, and the front wall 32 and the back wall 44 joined together along the side edges 34 and 46 by joining means, thereby forming two side fused edges 56 each side fused edge having respectively an upper end 58 located at or below the top edges and above the bottom edges and a lower end 60 located at the bottom edges, and forming an open mouth 62 defined by the two upper ends 58 and two upper unfused portions of the inner surfaces 40 and 52 lying between the two upper ends; and forming a writing tip opening 64 defined by the two lower ends 60 and two lower unfused portions of the inner surfaces 40 and 52 lying between the two lower ends.

The front wall 32 is defined by said front wall side edges 34, said front wall top edge 36, said front wall bottom edge 38, said front wall inner surface 40, and said front wall outer surface 42. The back wall 44 is defined by said back wall side edges 46, said back wall top edge 48, said back wall bottom edge 50, said back wall inner surface 52, and said back wall outer surface 54.

Figure 7:
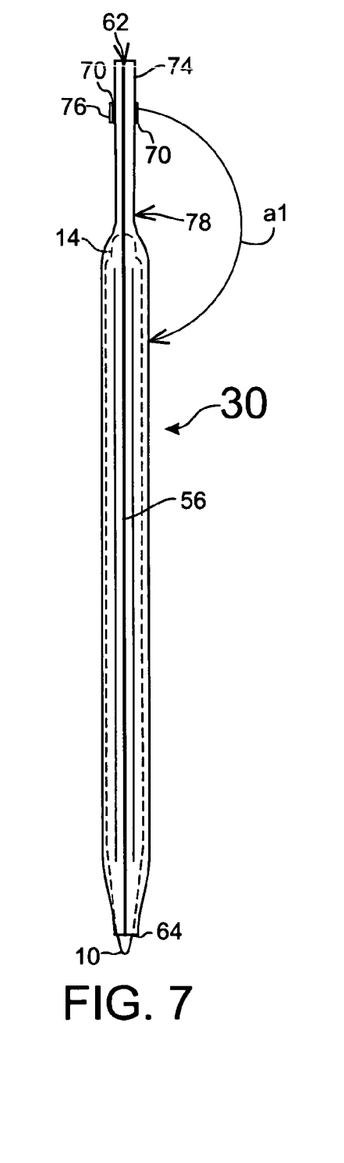
FIG. 7 is a side view of the writing utensil cover shown in FIG. 6 with a curved arrow a1 illustrating a direction in which a fold may be made in the writing utensil cover about the illustrated fold line and showing principally in outline the writing utensil enclosed within the writing utensil cover.

Preferably as illustrated in FIG. 7, the writing utensil cover 30 is longer than the writing utensil 8 that is to be used with the cover.

Preferably, the writing utensil cover 30 has a generally tubular shape and the open mouth 62 and the writing tip opening 64 are coaxial to each other about the longitudinal axis of the cover. Preferably, the open mouth 62 has a sectional width greater than a widest sectional width of a writing utensil 8 having a writing tip 10 that is to be used with the cover and the writing tip opening 64 has a sectional width greater than a widest sectional width of the writing tip and smaller than an intermediate sectional width of the writing utensil away from the writing tip and towards the widest section of the writing utensil.

Preferably, the writing utensil cover 30 has a first portion 66, the first portion having a first portion sectional width greater than a widest sectional width of the writing utensil 8, the first portion beginning at the open mouth 62 and extending towards the writing tip opening 64 and transitioning integrally into a second portion 68, the second portion having a tapering sectional width tapering down from the first portion sectional width to a sectional width of the writing tip opening and ending at the writing tip opening; the sectional width of the writing tip opening greater than a widest sectional width of the writing tip 10 and smaller than an intermediate sectional width of the tapered portion 12 away from the writing tip and towards the widest sectional width of the writing utensil.

Preferably, the second portion 68 is sized so as to snugly fit around the writing utensil 8 adjacent the writing tip 10 and the writing tip opening 64 allows passage of the writing tip through the writing tip opening and into an outside environment while the remainder of the writing utensil is still enclosed within the writing utensil cover.

Preferably, the two side fused edges 56 are of equal length and spaced from each other symmetrically about the parallel longitudinal axes of the walls 32 and 44.

Joining means include heat fusing, ultrasonic welding, or another suitable method of joining known in the art.

Preferably, as shown in FIGS. 1 through 4, an adhesive securing zone 70 that may have a removable protective strip 72 is deposed on at least one of the outer surfaces 42 and 54 near the open mouth 62 forming a gripping portion 74 in the outer surfaces between the open mouth and the adhesive securing zone or zones. The removable protective strip 72 may be removed prior to the use of the related adhesive securing zone 70.

Figures 1, 2, 3, 4, 5:
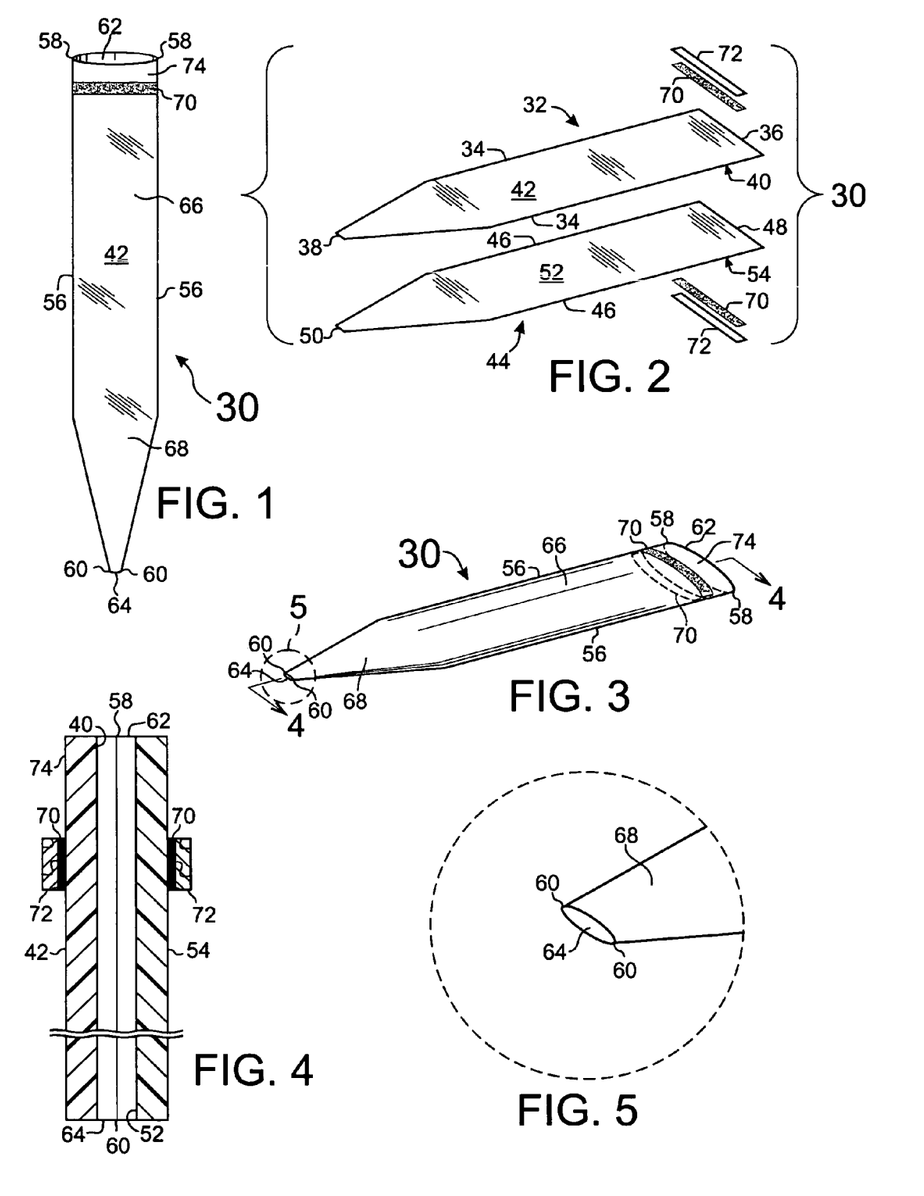
FIG. 1 is a perspective view of a writing utensil cover showing a preferred embodiment with an adhesive securing zone on an outer surface of a front wall.
FIG. 2 is an oblique exploded perspective view of a writing utensil cover showing the preferred embodiment.
FIG. 3 is an oblique perspective view of a writing utensil cover showing the preferred embodiment.
FIG. 4 is a partial sectional view of a writing utensil cover as viewed from direction 4—4 in FIG. 3.
FIG. 5 is an enlarged, partial view of the writing utensil cover as indicated in FIG. 3.
Figures 6, 8, 9:
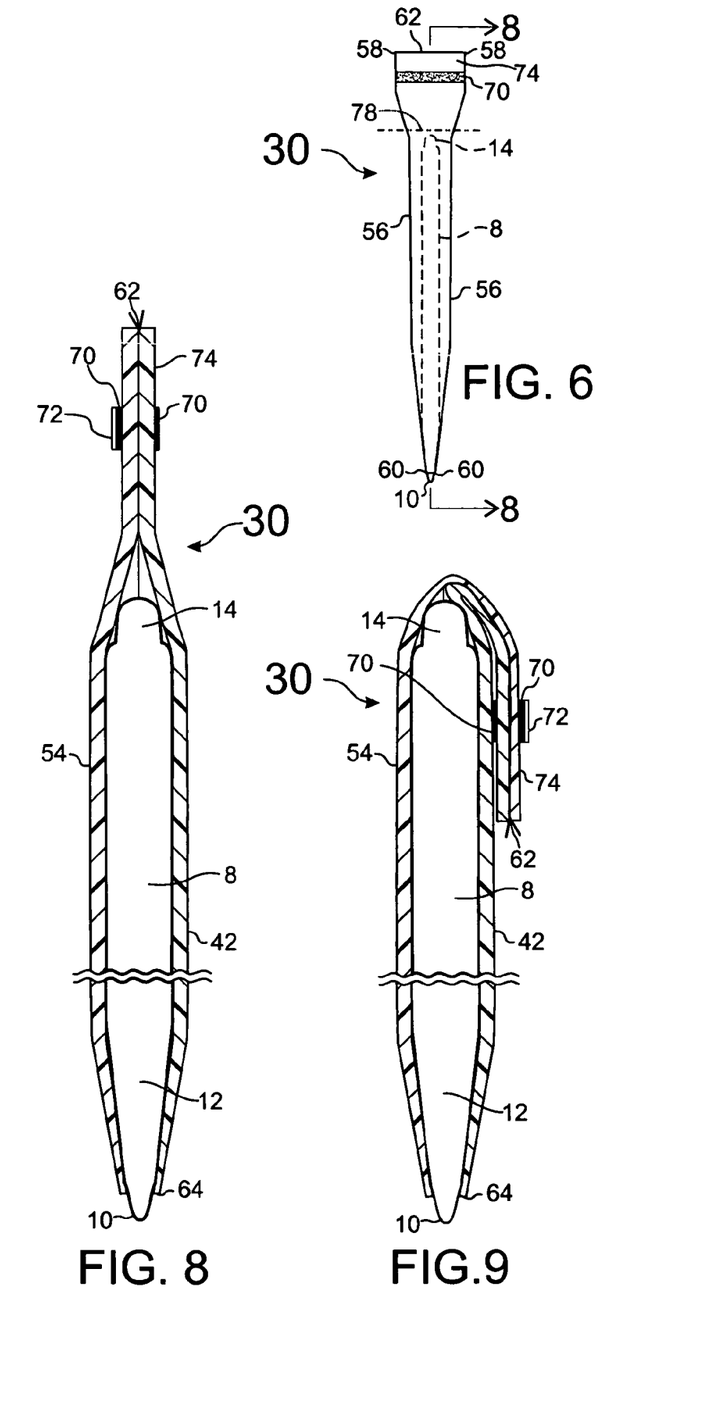
FIG. 6 is a front view of a writing utensil cover showing principally in outline a writing utensil having a writing tip and an opposite top end with the writing utensil enclosed except for the writing tip within the writing utensil cover and a transverse fold line.
FIG. 8 is a partial side cutaway view of the writing utensil cover shown in FIG. 7 showing the writing utensil enclosed except for the writing tip within the writing utensil cover and showing the writing tip extending out of the writing utensil cover through a writing tip opening.
FIG. 9 is a partial side cutaway view of the writing utensil cover shown in FIG. 8 showing the writing utensil cover folded over onto itself and with a portion of the writing utensil cover secured by an adhesive securing zone to a portion of the outer surface of the writing utensil cover.

As illustrated in FIGS. 6 and 9, closure of a writing utensil cover 30 in the preferred embodiment is effected after a writing utensil 8 having a writing tip 10 and an opposite top end 14 is first fully inserted into the cover and seated in close engagement in the cover with the writing tip extending out through a writing tip opening 64, the cover is then folded along a transverse fold line 78 located transverse to the longitudinal axis of the cover and above the opposite top end and by securing an adhesive securing zone 70 to an outer surface 42 or 54 below the opposite top end and towards the writing tip opening. The direction of the folding is indicated in FIG. 7 by arrow a1. FIG. 9 shows an adhesive securing zone 70 secured to an outer surface 42.

Figure 10:
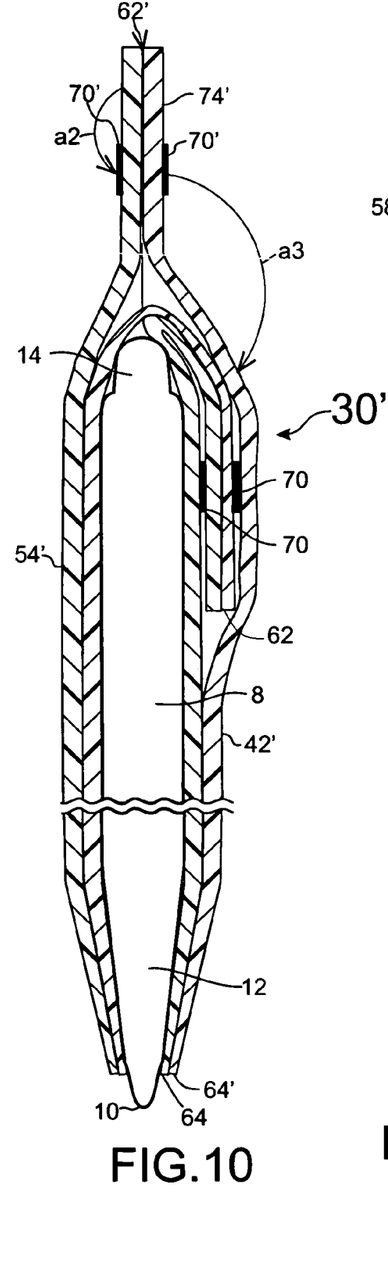
FIG. 10 is a partial side cutaway view of a plurality of writing utensil covers and showing a writing utensil, having a writing tip and an opposite top end, with the writing utensil enclosed except for the writing tip within a first writing utensil cover and the first writing utensil cover inserted within another writing utensil cover and showing two curved arrows a2 and a3 illustrating two directions in which two folds may be made in the second writing utensil cover.

As shown in FIG. 10, a writing utensil 8 that is enclosed in a first writing utensil cover 30 may together with the first writing utensil cover be inserted and nested in another writing utensil cover 30'. The second writing utensil cover 30' may be a duplicate of writing utensil cover 30 or it may be slightly larger than cover 30 and thus the elements of writing utensil cover 30' shown in FIG. 10 as 42', 54', 62', 64', 70', and 74' are distinguished from similar elements 42, 54, 62, 64, 70, and 74 of writing utensil cover 30 by the use of single prime marks with the reference numbers.

In FIG. 10, arrow a2 shows a direction that a portion of the writing utensil cover 30' above two adhesive securing zones 70' may be folded to secure a portion of an outer surface 54' to one of the adhesive securing zones and an arrow a3 shows a direction that the writing utensil cover 30' may be folded down onto itself to secure the other adhesive securing zone to a portion of an outer surface 42' at a point below the opposite top end 14 and towards the writing tip 10.

Figure 11:
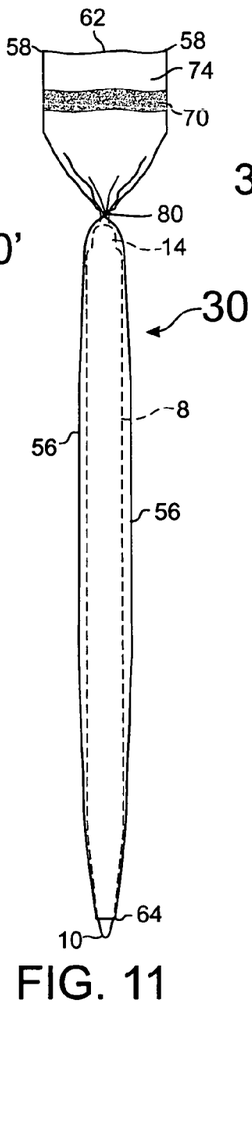
FIG. 11 is a front view of a writing utensil cover showing principally in outline a writing utensil having a writing tip and an opposite top end with the writing utensil enclosed except for the writing tip within the writing utensil cover and showing a twisted portion of the writing utensil cover about its longitudinal axis above the opposite top end whereby the writing utensil cover snugs down about and around the writing utensil.
Figure 12:
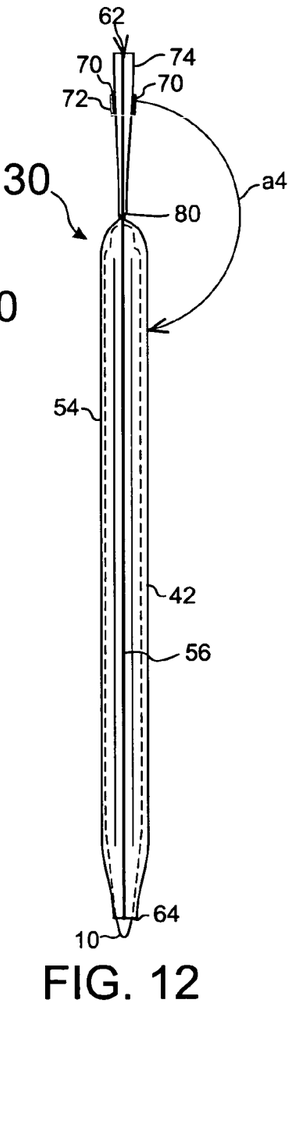
FIG. 12 is a side view of the writing utensil cover shown in FIG. 11 with a curved arrow a4 illustrating a direction in which a fold may be made in the writing utensil cover.

FIG. 11 helps illustrate a method of closure of a writing utensil cover 30 where after insertion of a writing utensil 8 into the cover, a portion of the cover above the opposite top end 14 is twisted about the longitudinal axis of the cover forming a twisted portion 80 that snugs down the cover about and around the writing utensil. FIG. 12 helps illustrate with a curved arrow a4 a direction in which a fold of the cover above the opposite top end 14 may be made over onto itself to secure an adhesive securing zone 70 to the front wall outer surface 42 at a point below the opposite top end and towards the writing tip 10.

FIGS. 13 to 21 show a writing utensil cover 130 which is a second embodiment of the writing utensil cover that differs from the first embodiment by the replacement of the back wall 44 of the first embodiment with a longer back wall 144 having a back wall bottom edge 50, two back wall side edges 146, a back wall inner surface 152, a back wall outer surface 154, and a back wall top edge 148. The two back wall side edges 146, the back wall inner surface 152, and the back wall outer surface 154 are longer than the front wall side edges 34, the front wall inner surface 40, and the front wall outer surface 42 of the first embodiment resulting in a back wall flap portion 82 that extends the back wall beyond the overlying front wall 32 and the front wall top edge 36 to the back wall top edge 148. The back wall bottom edge 50 is the same as the back wall bottom edge 50 in the first embodiment.

Figures 13, 14, 15, 16, 17:
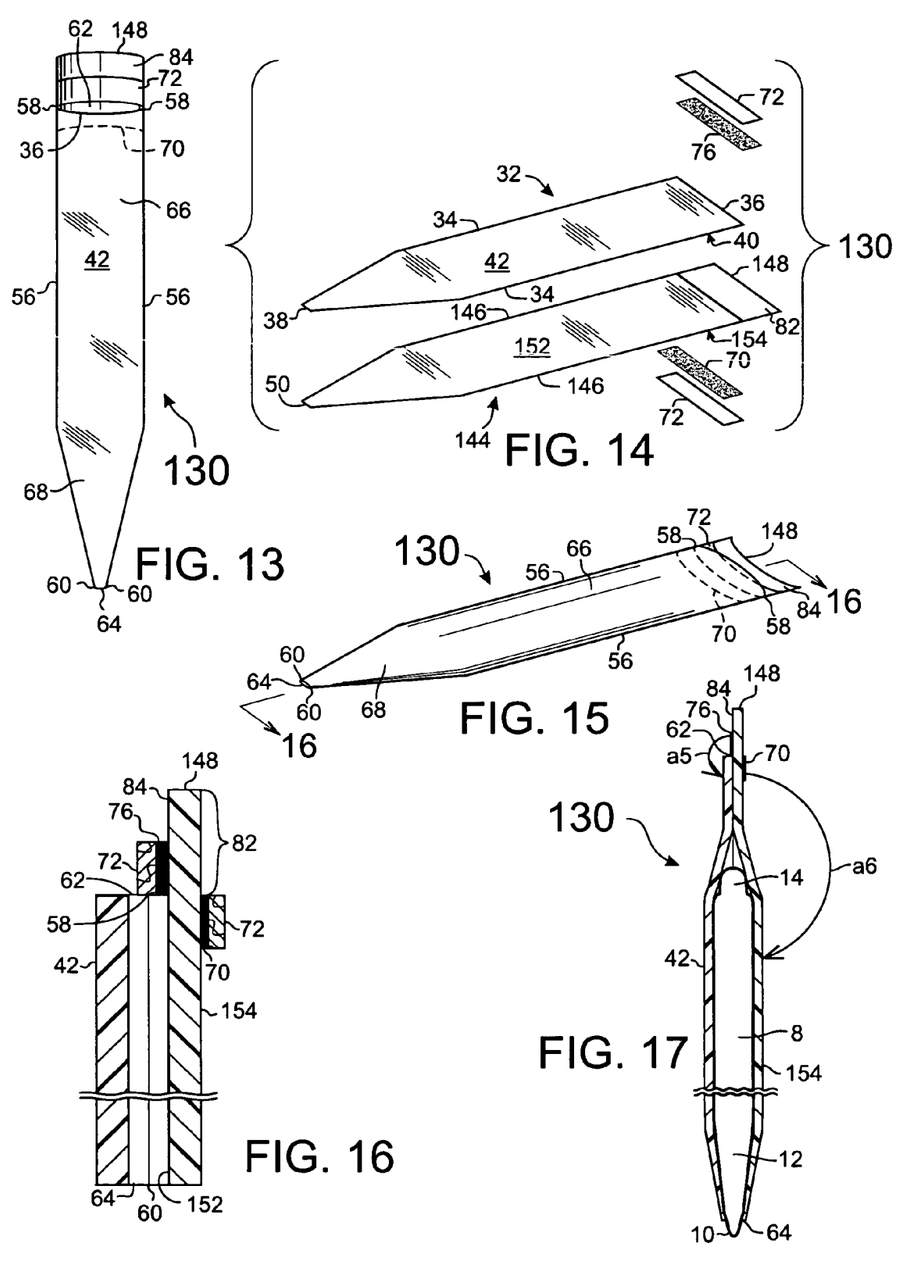
FIG. 13 is a perspective view of a writing utensil cover showing a second embodiment with an adhesive closure zone on an inner surface of a back wall flap portion.
FIG. 14 is an oblique exploded perspective view of a writing utensil cover showing a second embodiment and showing a back wall flap portion.
FIG. 15 is an oblique perspective view of a writing utensil cover showing a second embodiment.
FIG. 16 is a partial sectional view of a writing utensil cover as viewed from direction 16—16 in FIG. 15.
FIG. 17 is a partial side cutaway view of a writing utensil cover showing a second embodiment, showing a writing utensil having a writing tip enclosed except for the writing tip within the writing utensil cover, showing the writing tip extending out of the writing utensil cover through a writing tip opening, showing a back wall flap portion, showing a small curved arrow a5 illustrating a direction in which a fold may be made in the back wall flap portion over onto an outer surface of a front wall of the writing utensil cover, and showing a larger curved arrow a6 illustrating a direction in which a fold may be made in the writing utensil cover.

As shown in FIG. 16, in the second embodiment, preferably, an adhesive closure zone 76 is deposed transversely on a portion of the back wall inner surface 152 that is part of the back wall flap portion 82 immediately above the top ends 58 and spaced down from the back wall top edge 148 forming a back wall gripping lip portion 84 immediately below the back wall top edge and an adhesive securing zone 70 is deposed transversely on the back wall outer surface 154 immediately below the top ends. As shown in FIGS. 13 to 16, a removable protective strip 72 may be placed on the adhesive closure zone 76 and as shown in FIGS. 14 and 16 on the adhesive securing zone 70.

As shown in FIGS. 17 through 21, the writing utensil cover 130 is closed after a writing utensil 8 is inserted into the cover with the writing tip 10 extending out of the cover through the writing tip opening 64 by folding the back wall flap portion 82 over as far as possible onto the front wall outer surface 42 and securing the back wall flap portion to the overlain surfaces with an adhesive closure zone 76. The direction of the fold of the back wall flap portion 82 is shown by arrow a5 in FIG. 17 and by arrow a7 in FIG. 19.

In FIG. 17, a second arrow a6 shows a direction that an upper portion of the writing utensil cover 130 may be folded to secure an adhesive securing zone 70 to a portion of back wall outer surface 154 below the opposite top end 14.

Figure 18:
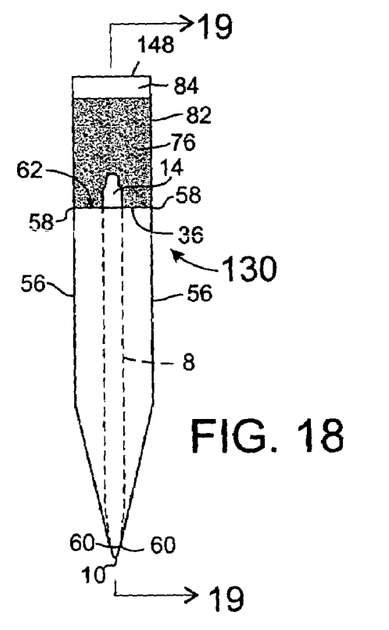
FIG. 18 is a front view of a writing utensil cover showing a second embodiment in an open condition showing a writing utensil having a writing tip and an opposite top end with the writing utensil enclosed except for the writing tip and the opposite top end within the writing utensil cover.
Figure 19:
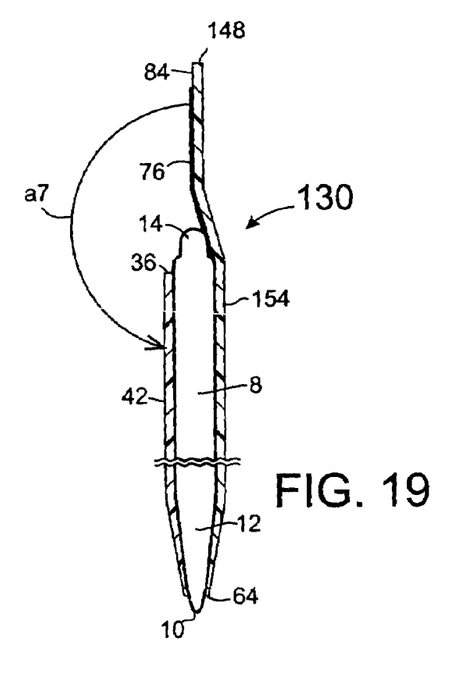
FIG. 19 is a partial side cutaway view of the writing utensil cover shown in FIG. 18 with a curved arrow a7 illustrating a direction in which a transverse fold may be made in the writing Utensil cover over the opposite top end of the writing utensil thereby enclosing the writing utensil except for the writing tip.

FIGS. 18 and 19 show a writing utensil cover 130 in an open condition with a writing utensil 8 inserted into the cover and the back wall flap portion 82 ready to be folded in the direction shown by arrow a7 in FIG. 19.

Figure 20:
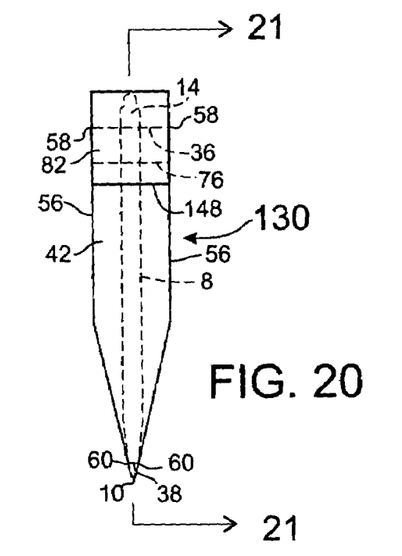
FIG. 20 is a front view of the writing utensil cover shown in FIG. 18 in a closed condition.
Figure 21:
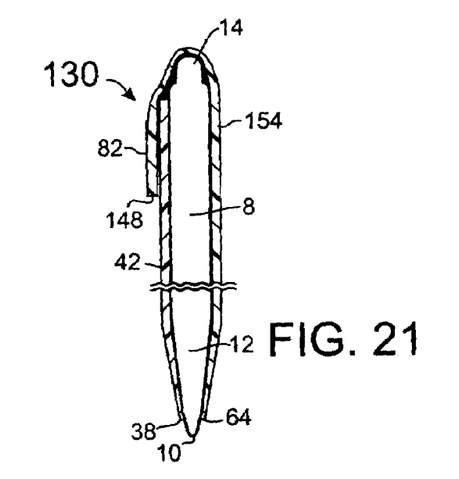
FIG. 21 is a partial side cutaway view of the writing utensil cover as viewed from direction 21—21 in FIG. 20.

FIGS. 20 and 21 show the writing utensil cover 130 in a closed condition with the back wall flap portion 82 folded over as far as possible onto the front wall outer surface 42 with an adhesive closure zone 76 securing a portion of the back wall flap portion to a portion of the front wall outer surface below the front wall top edge 36 and towards the front wall bottom edge 38 and securing a portion of the adhesive closure zone to another portion of the adhesive closure zone.

FIGS. 22 to 25 show a writing utensil cover 230 which is a third embodiment of the writing utensil cover that differs from the second embodiment 130 by further comprising a front wall flap portion 86 having a front wall flap portion bottom edge 138 joined along the front wall flap portion bottom edge to the front wall top edge 36 of the front wall 32. The front wall flap portion 86 has a front wall flap portion bottom edge 138, two front wall flap portion side edges 134, a front wall flap portion top edge 136, a front wall flap portion inner surface 140, and a front wall flap portion outer surface 142. The front wall flap portion 86 overlies the back wall flap portion 82. Preferably, in the third embodiment, the front wall flap portion 86 may be integral to the front wall 32.

Figures 22, 23, 24, 25:
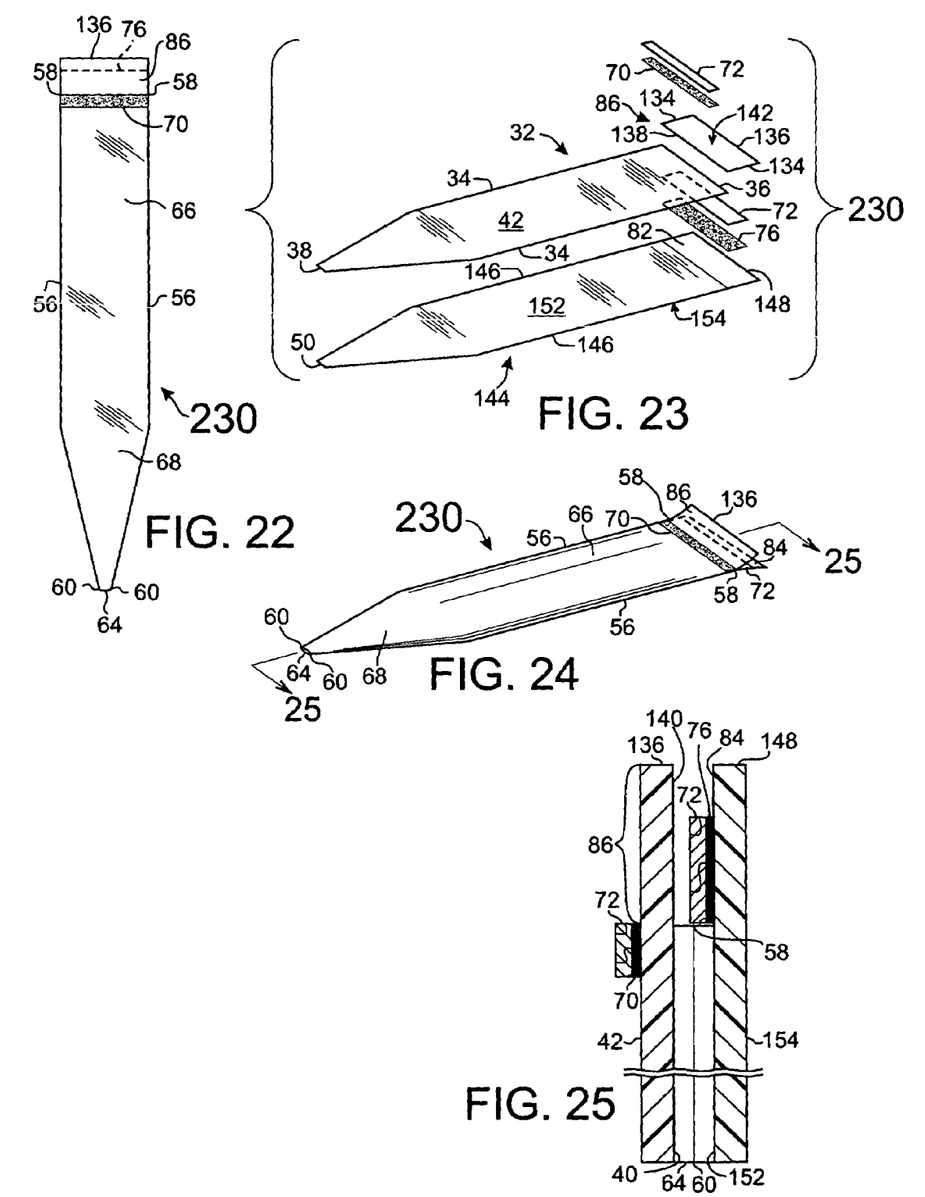
FIG. 22 is a perspective view of a writing utensil cover showing a third embodiment with an adhesive securing zone on an outer surface of a front wall.
FIG. 23 is an oblique exploded perspective view of a writing utensil cover showing a third embodiment and showing a front wall flap portion and a back wall flap portion.
FIG. 24 is an oblique perspective view of a writing utensil cover showing a third embodiment.
FIG. 25 is a partial sectional view of a writing utensil cover as viewed from direction 25—25 in FIG. 24.

As shown in FIG. 25, in the third embodiment, preferably, an adhesive closure zone 76 is deposed transversely on a portion of the back wall inner surface 152 that is part of the back wall flap portion 82 immediately above the top ends 58 and spaced down from the back wall top edge 148 forming a back wall gripping lip portion 84 uncovered by adhesive immediately below the back wall top edge and an adhesive securing zone 70 is deposed transversely on the front wall outer surface 42 immediately below the top ends.

As shown in FIGS. 23 to 25, a removable protective strip 72 may be placed on the adhesive closure zone 76 and as shown in FIGS. 23 and 25 on the adhesive securing zone 70.

Preferably, the writing utensil cover 230 is used with a writing utensil 8 that can be fully inserted writing tip 10 first into the cover and with the opposite top end 14 located in the cover below the upper ends 58 and the cover is then closed by securing the adhesive closure zone 76 on the back wall flap portion inner surface 152 to the overlying front wall flap portion inner surface 140. The writing utensil cover 230 has a front wall gripping lip portion 88 immediately below the front wall flap portion top edge 136.

Figure 26:
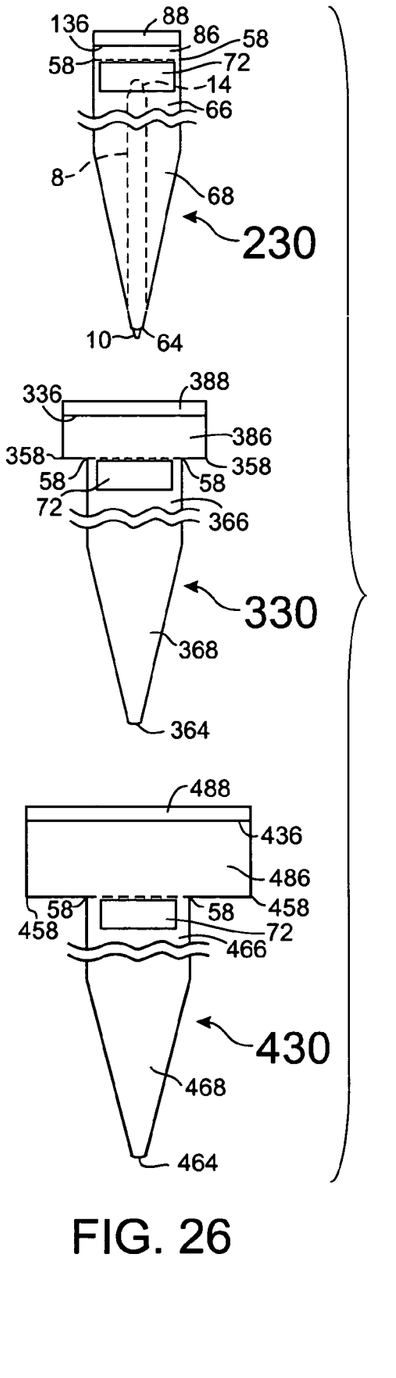
FIG. 26 is a partially exploded partial view of a plurality of nesting writing utensil covers showing a writing utensil, an inner writing utensil cover, an intermediate writing utensil cover, and an outer writing utensil cover.

FIG. 26 shows a partially exploded partial view of a writing utensil and a plurality of nesting writing utensil covers with the writing utensil inserted into an inner writing utensil cover 230, an intermediate writing utensil cover 330, and an outer writing utensil cover 430. More than one intermediate writing utensil cover may be used, nested, and interposed between the inner writing utensil cover 230 and the outer writing utensil cover 430.

The intermediate writing utensil cover 330 differs from the inner writing utensil cover 230 by having a slightly wider first portion 366, a slightly wider second portion 368, a wider and taller front wall flap portion 386 that extends laterally and symmetrically outward away from the two upper ends 58 to two side ends 358 spaced away from the longitudinal axis of the cover, the front wall flap portion overlies a similar sized back wall flap portion 382 that extends laterally and symmetrically outward away from the two upper ends 58 to two side ends 358 spaced away from the longitudinal axis of the cover, the flap portions are joined together along the two portions of their overlying edges that lie outward from the longitudinal axis and opposite their top edges 336 and 348 and lie respectively between an upper end 58 outward to a corresponding side end 358 as shown in FIG. 26.

The intermediate writing utensil cover 330, preferably has an adhesive closure zone 376 wider and taller than the adhesive closure zone 76 of the cover 230 with the adhesive closure zone deposed on the back wall flap portion inner surface 352 immediately above the top ends 58 and the side ends 358 and spaced from the back wall flap portion top edge 348 forming a back wall gripping lip portion 384 uncovered by adhesive and located between the adhesive closure zone and the back wall flap portion top edge 348. The overlying front wall flap portion 386 has a front wall gripping lip portion 388 on the front wall flap portion inner surface 340 and immediately below the front wall flap portion top edge 336.

The outer writing utensil cover 430 differs from the intermediate writing utensil cover 330 by having a slightly wider first portion 466, a slightly wider second portion 468, a wider and taller front wall flap portion 486, a that extends laterally and symmetrically outward away from the two upper ends 58 to two side ends 458 spaced away from the longitudinal axis of the cover, the front wall flap portion overlies a similar sized back wall flap portion 482 that extends laterally and symmetrically outward away from the two upper ends 58 to two side ends 458 spaced away from the longitudinal axis of the cover, the flap portions are joined together along the two portions of their overlying edges that lie outward from the longitudinal axis and opposite their top edges 436 and 448 and lie respectively between an upper end 58 outward to a corresponding side end 458 as shown in FIG. 26.

The outer writing utensil cover 430, preferably has an adhesive closure zone 476 wider and taller than the adhesive closure zone 376 of the cover 330 with the adhesive closure zone deposed on the back wall flap portion inner surface 452 immediately above the top ends 58 and the side ends 458 and spaced from the back wall flap portion top edge 448 forming a back wall gripping lip portion 484 uncovered by adhesive and located between the adhesive closure zone and the back wall flap portion top edge 448. The overlying front wall flap portion 486 has a front wall gripping lip portion 488 on the front wall flap portion inner surface 440 and immediately below the front wall flap portion top edge 436.

Figure 27:
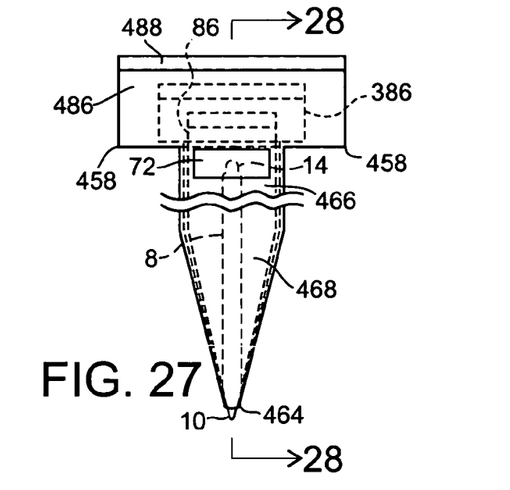
FIG. 27 is a partial front view of a writing utensil and a plurality of nesting writing utensil covers shown in FIG. 26 after being nested together with the writing utensil inserted into an inner writing utensil cover; the inner writing utensil cover and the writing utensil nesting within an intermediate writing utensil cover; and the intermediate writing utensil cover, the inner writing utensil cover, and the writing utensil nesting within an outer writing utensil cover and showing principally in outline a writing utensil having a writing tip and an opposite top end enclosed except for the writing tip within the plurality of nesting writing utensil covers.
Figure 28:
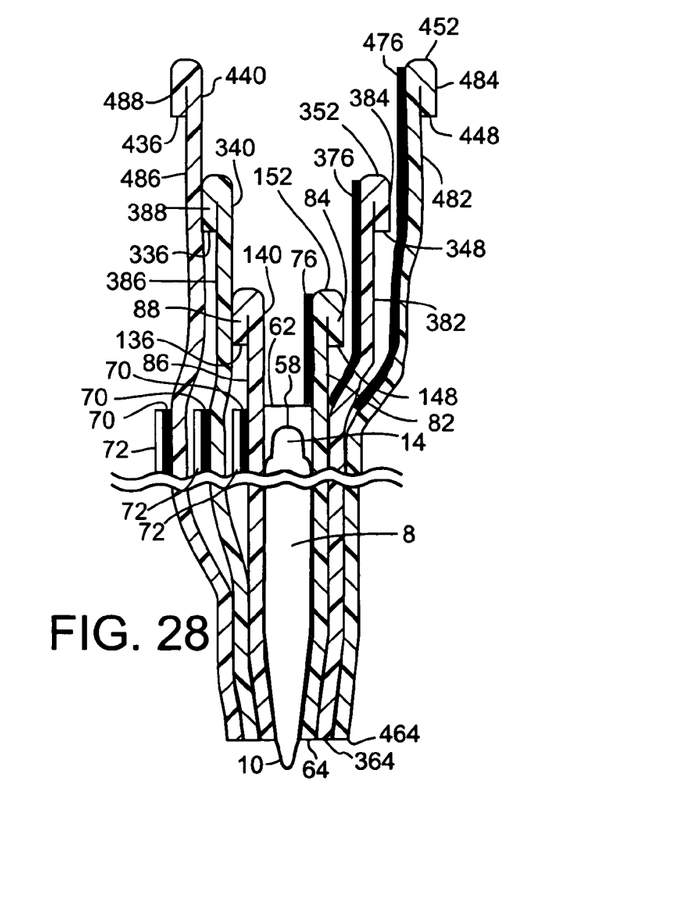
FIG. 28 is a partial side cutaway view of a writing utensil and a plurality of nesting writing utensil covers after being nested together showing the writing utensil and the plurality as viewed from direction 28—28 in FIG. 27 (the covers are shown open).

FIGS. 26 to 28 show how in a preferred method of use, a writing utensil and a plurality of nesting writing utensil covers nest like Russian Babushka dolls with the writing utensil inserted into an inner writing utensil cover 230; the inner writing utensil cover and the writing utensil nesting within an intermediate writing utensil cover 330; and the intermediate writing utensil cover, the inner writing utensil cover, and the writing utensil nesting within an outer writing utensil cover 430.

As illuminated in FIGS. 24 to 28, a preferred method of use of a writing utensil with a plurality of writing utensil covers may include the following steps:

a) selecting a writing utensil 8 having a writing tip 10 and an opposite top end 14;
b) inserting the writing utensil into an inner writing utensil cover 230 having a writing tip opening 64 with the writing tip extending out through the writing tip opening;
c) closing the inner writing utensil cover by securing an adhesive closure zone 76 on a back wall flap portion inner surface 152 to a front wall flap portion inner surface 140;
d) nesting the inner writing utensil cover and the writing utensil into an intermediate writing utensil cover 330 having a second writing tip opening 364 with the writing tip extending out through the second writing tip opening;
e) closing the intermediate writing utensil cover by securing an adhesive closure zone 376 on a back wall flap portion inner surface 352 to a front wall flap portion inner surface 340;
f) nesting the intermediate writing utensil cover, the inner writing utensil cover, and the writing utensil into an outer writing utensil cover 430 having a third writing tip opening 464 with the writing tip extending out through the third writing tip opening;
g) closing the outer writing utensil cover by securing an adhesive closure zone 476 on a back wall flap portion inner surface 452 to a front wall flap portion inner surface 440;
h) using the writing utensil in a first environment;
i) removing and discarding the outer writing utensil cover;
j) using the writing utensil in a second environment;
k) removing and discarding the intermediate writing utensil cover;
l) using the writing utensil in a third environment; and
m) removing and discarding the inner writing utensil cover.

A user may choose to utilize only two nested writing utensil covers with a writing utensil and in such a situation, the method of use may include the following steps:

a) selecting a writing utensil having a writing tip and an opposite top end;
b) inserting the writing utensil into a first writing utensil cover having a writing tip opening with the writing tip extending out through the writing tip opening;
c) closing the first writing utensil cover;
d) nesting the first writing utensil cover and the writing utensil into a second writing utensil cover having a second writing tip opening with the writing tip extending out through the second writing tip opening;
e) closing the second writing utensil cover;
f) using the writing utensil in a first environment;
g) removing and discarding the second writing utensil cover;
h) using the writing utensil in a second environment; and
i) removing and discarding the first writing utensil cover.

Preferably, a writing utensil cover after manufacture is sterile and is individually packaged within a sterile outer packaging element (not shown) to await its use with a writing utensil. A plurality of nesting covers may also be packaged as a group for use. The writing utensil covers may also be dispensed in a nonsterile manner on a perforated roll with the covers side by side or end to end with a cover first separated from the roll prior to its use with a writing utensil.

A plurality of writing utensil covers may be used wherein a writing utensil is fully inserted into a first cover which is then closed over the writing utensil except for its writing tip, then another cover is placed over the first cover and the writing utensil, and then additional covers may be placed sequentially over the preceding covers and the writing utensil as desired to form a multilayer system with as many layers as desired to provide enhanced protection against contamination to or from a writing utensil.

Preferably, either the front wall or the back wall of a writing utensil cover is colored white and may also be opaque and the other wall is transparent so as to more readily allow a user to discern whether visible contamination of the writing utensil cover has occurred during use.

The writing utensil covers 30, 30', 130, 230, 330, and 430 may be made from any suitable thin walled flexible material such as thermoplastic, polyethylene, polypropylene, or polyester films including Mylar™ films, synthetic rubber, silicone, or latex or any other material that will remain impervious to the transmission of contamination through the material. Preferably the covers are made out of a plastic film such as polyethylene.

The adhesive securing zones 70 and 70' and the adhesive closure zones 76, 376, and 476 may be made of pressure-sensitive adhesive materials including acrylic, natural, and synthetic rubber types. Preferably, an adhesive material having good peel strength is used.

The preceding description and exposition of the invention is presented for purposes of illustration and enabling disclosure. It is neither intended to be exhaustive nor to limit the invention to the precise forms disclosed. Modifications or variations in the invention in light of the above teachings that are obvious to one of ordinary skill in the art are considered within the scope of the invention as determined by the appended claims when interpreted to the breath to which they fairly, legitimately and equitably are entitled.

What is claimed is:

1. A writing utensil cover in combination with a writing utensil, said writing utensil having a writing tip, a tapered portion adjacent said writing tip with said tapered portion increasing in cross sectional width away from said writing tip, and an opposite top end, wherein said cover comprises:

a front wall having two front wall side edges, a front wall top edge, a front wall bottom edge, a front wall inner surface, and a front wall outer surface;

said front wall overlying a back wall having two back wall side edges, a back wall top edge, a back wall bottom edge, a back wall inner surface, and a back wall outer surface;

said front wall and said back wall aligned in facing relationship with said front wall bottom edge overlying said back wall bottom edge, said front wall side edges overlying said back wall side edges, and said front wall inner surface facing and overlying said back wall inner surface;

said front wall and said back wall joined together along said side edges by joining means, thereby forming two side fused edges;

each said side fused edge having respectively an upper end and a lower end;

each said upper end located at said top edges and each said lower end located at said bottom edges;

an open mouth defined by said two upper ends and two upper unfused portions of said inner surfaces and lying between said two upper ends;

a writing tip opening defined by said two lower ends and two lower unfused portions of said inner surfaces and lying between said two lower ends; and a first portion, said first portion having a first portion sectional width greater than a widest sectional width of said writing utensil, said first portion beginning at said open mouth and extending towards said writing tip opening and transitioning integrally into a second portion, said second portion having a tapering sectional width tapering down from said first portion sectional width to a sectional width of said writing tip opening and ending at said writing tip opening; said sectional width of said writing tip opening greater than a widest sectional width of said writing tip and smaller than an intermediate sectional width of said tapered portion away from said writing tip and towards said widest sectional width of said writing utensil.

2. A writing utensil cover according to claim 1 wherein said joining means include heat fusing, ultrasonic welding, or another suitable method of joining known in the art.

3. A writing utensil cover according to claim 1 further comprising an adhesive securing zone, said adhesive securing zone deposed on at least one of said outer surfaces near said open mouth.

4. A writing utensil cover according to claim 1 further comprising a back wall flap portion, said back wall flap portion extending said back wall beyond said overlying front wall.

5. A writing utensil cover according to claim 4 further comprising an adhesive closure zone, said adhesive closure zone deposed on a portion of said back wall inner surface that is a part of said back wall flap portion immediately above said top ends.

6. A writing utensil cover according to claim 5 further comprising a front wall flap portion, said front wall flap portion having a front wall flap portion bottom edge, two front wall flap portion side edges, a front wall flap portion top edge, a front wall flap portion inner surface, and a front wall flap portion outer surface, said front wall flap portion joined along said front wall flap portion bottom edge to said front wall top edge, and said front wall flap portion overlying said back wall flap portion.

7. A writing utensil cover according to claim 1 wherein either said front wall or said back wall is colored white and the other said front wall or said back wall is transparent.

8. A writing utensil cover in combination with a writing utensil, said writing utensil having a writing tip, a tapered portion adjacent said writing tip with said tapered portion increasing in cross sectional width away from said writing tip, and an opposite top end, wherein said cover comprises:

a front wall having two front wall side edges, a front wall top edge, a front wall bottom edge, a front wall inner surface, and a front wall outer surface;

said front wall overlying a back wall having two back wall side edges, a back wall top edge, a back wall bottom edge, a back wall inner surface, and a back wall outer surface;

said front wall and said back wall aligned in facing relationship with said front wall bottom edge overlying said back wall bottom edge, said front wall side edges overlying said back wall side edges, and said front wall inner surface facing and overlying said back wall inner surface;

said front wall and said back wall joined together along said side edges by joining means, thereby forming two side fused edges;

each said side fused edge having respectively an upper end and a lower end;

each said upper end located below said top edges and above said bottom edges and each said lower end located at said bottom edges;

an open mouth defined by said two upper ends and two upper unfused portions of said inner surfaces and lying between said two upper ends;

a writing tip opening defined by said two lower ends and two lower unfused portions of said inner surfaces and lying between said two lower ends; and a first portion, said first portion having a first portion sectional width greater than a widest sectional width of said writing utensil, said first portion beginning at said open mouth and extending towards said writing tip opening and transitioning integrally into a second portion, said second portion having a tapering sectional width tapering down from said first portion sectional width to a sectional width of said writing tip opening and ending at said writing tip opening; said sectional width of said writing tip opening greater than a widest sectional width of said writing tip and smaller than an intermediate sectional width of said tapered portion away from said writing tip and towards said widest sectional width of said writing utensil.

9. A writing utensil cover according to claim 8 wherein said joining means include heat fusing, ultrasonic welding, or another suitable method of joining known in the art.

10. A writing utensil cover according to claim 8 further comprising an adhesive securing zone, said adhesive securing zone deposed on at least one of said outer surfaces near said open mouth.

11. A writing utensil cover according to claim 8 further comprising a back wall flap portion, said back wall flap portion extending said back wall beyond said overlying front wall.

12. A writing utensil cover according to claim 11 further comprising an adhesive closure zone, said adhesive closure zone deposed on a portion of said back wall inner surface that is a part of said back wall flap portion immediately above said top ends.

13. A writing utensil cover according to claim 12 further comprising a front wall flap portion, said front wall flap portion having a front wall flap portion bottom edge, two front wall flap portion side edges, a front wall flap portion top edge, a front wall flap portion inner surface, and a front wall flap portion outer surface, said front wall flap portion joined along said front wall flap portion bottom edge to said front wall top edge, and said front wall flap portion overlying said back wall flap portion.

* * * * *